(12) United States Patent
Schlipper

(10) Patent No.: US 9,161,596 B2
(45) Date of Patent: Oct. 20, 2015

(54) SECURITY LUGGAGE BAG

(71) Applicant: MRM HK LTD, Hong Kong (HK)

(72) Inventor: Robert Wesley Schlipper, Hong Kong (HK)

(73) Assignee: MRM HK Ltd., Hong Kong (HK)

( * ) Notice: Subject to any disclaimer, the term of this patent is extended or adjusted under 35 U.S.C. 154(b) by 0 days.

(21) Appl. No.: 13/694,922

(22) Filed: Jan. 18, 2013

(65) Prior Publication Data

US 2014/0090942 A1   Apr. 3, 2014
US 2015/0216275 A9   Aug. 6, 2015

Related U.S. Application Data

(63) Continuation-in-part of application No. 11/337,839, filed on May 1, 2006.

(30) Foreign Application Priority Data

Jan. 18, 2012 (AU) ................................ 2012900188

(51) Int. Cl.
*A45C 13/18* (2006.01)
*A45C 5/02* (2006.01)
*A45C 3/00* (2006.01)
*A61B 17/04* (2006.01)
*D05B 1/12* (2006.01)
*D05B 93/00* (2006.01)
*A41D 31/00* (2006.01)

(52) U.S. Cl.
CPC . *A45C 5/02* (2013.01); *A45C 3/001* (2013.01); *A45C 13/18* (2013.01); *A61B 17/0401* (2013.01); *D05B 1/12* (2013.01); *D05B 93/00* (2013.01); *A41D 31/0055* (2013.01); *A45C 2003/002* (2013.01); *Y10T 428/2481* (2015.01)

(58) Field of Classification Search
CPC .. A45C 3/001; A45C 2003/002; A45C 13/18; A41D 31/055
USPC .......... 190/101, 107, 125, 127; 150/101, 102, 150/129, 130, 134; 428/197
See application file for complete search history.

(56) References Cited

U.S. PATENT DOCUMENTS

| | | | | | |
|---|---|---|---|---|---|
| 276,240 | A | * | 4/1883 | Hallidie | 190/125 |
| 1,172,708 | A | * | 2/1916 | Hoard | 190/125 |
| 3,085,259 | A | * | 4/1963 | Sandor | 5/247 |
| 4,610,334 | A | * | 9/1986 | Pelavin | 190/122 |
| 4,907,728 | A | * | 3/1990 | Giblet | 224/585 |
| 5,213,874 | A | * | 5/1993 | Prudhomme | 428/198 |
| 6,026,662 | A | | 2/2000 | Schlipper | |
| 6,067,911 | A | * | 5/2000 | Marker et al. | 105/15 |
| 6,244,081 | B1 | | 6/2001 | Schlipper | |
| 6,431,504 | B1 | * | 8/2002 | Ignagni | 248/118.5 |

(Continued)

FOREIGN PATENT DOCUMENTS

| AU | 695896 B1 | 8/1998 |
|---|---|---|
| AU | 9863585 B | 8/1998 |

(Continued)

*Primary Examiner* — Sue A Weaver
(74) *Attorney, Agent, or Firm* — Faegre Baker Daniels LLP

(57) ABSTRACT

A security luggage bag having multi layered walls defining a storage volume and at least one of the walls has a reinforcing layer comprised of a fabric with a reinforcing wire strand on a surface of the fabric, the reinforcing strand being fixed to the fabric as with stitching, tape or welds extending lengthwise along the reinforcing strand.

16 Claims, 4 Drawing Sheets

(56) References Cited

U.S. PATENT DOCUMENTS

| | | | |
|---|---|---|---|
| 6,463,771 B1 * | 10/2002 | Judge | 70/68 |
| 6,880,583 B2 * | 4/2005 | Billings | 139/383 AA |
| 7,661,223 B2 * | 2/2010 | Dudney | 43/26 |
| 7,853,599 B2 * | 12/2010 | Liu et al. | 707/748 |
| 2003/0110818 A1 | 6/2003 | Schlipper | |
| 2006/0180619 A1 | 8/2006 | Schlipper | |
| 2010/0243114 A1 * | 9/2010 | Hai et al. | 150/102 |

FOREIGN PATENT DOCUMENTS

| | | |
|---|---|---|
| AU | 2002300422 B2 | 6/2003 |
| AU | 2003200338 A1 | 8/2003 |
| CN | 103213335 A | 7/2013 |
| DE | 2722436 A1 | 11/1978 |
| EP | 0408522 A2 | 1/1991 |
| EP | 0878143 B1 | 2/2002 |
| EP | 1688059 B1 | 8/2006 |
| FR | 760606 A | 2/1934 |
| GB | 162091 A | 4/1921 |
| GB | 884959 A | 4/1958 |
| GB | 2031375 A | 4/1980 |

* cited by examiner

SECURITY LUGGAGE BAG

REFERENCE TO RELATED APPLICATIONS

This application is a continuation in part to my application Ser. No. 11/337,839, Filed: May 1, 2006.

Applicant claims the benefit of Australian Provisional Patent Application No. 2012900188, Filed Jan. 18, 2012

BACKGROUND OF THE INVENTION

1. Field of the Invention

The present invention relates to a softside luggage bag having a reinforced cover defining the storage volume thereof and in which the cover is resistant to being sliced open by anyone attempting to steal or surreptitiously remove the contents of the luggage bag through such a sliced opening. Ads utilized herein, the term "luggage bag" is defined to include all forms of storage bags which are generally carried by the user, often during traveling, and utilized for temporarily retaining in the volume various articles and items and includes, but is not limited to, backpacks, suitcases, shoulder bags, Gladstone bags, duffle bags, purses, brief cases, computer or other electronic device cases, and the like.

2. Background of the Invention

The use of reinforcement such as a flexible wire mesh in the cover of flexible or softside luggage bags provides an increased level of security against theft, particularly that which achieved by some unauthorized person slicing open the bag and stealing the contents of the storage volume. The mesh can be held adjacent the fabric or other flexible material walls of the luggage bag for greatly enhanced security, while still retaining the advantages of traditional softside un-reinforced products. For luggage bags of this construction, it is convenient to have a fabric outer layer providing, if desired, a waterproof shell about the mesh layer. To prevent the bag's contents snagging, or being damaged by the wire mesh layer exposed on the inside, a liner, such as an inner fabric layer is used and the inner fabric layer is typically of relatively lighter material than the outer fabric layer.

The wire mesh layer may be formed in the shape of the bag from a single wire strand arrayed in a preselected pattern, or from separate sheets of the cover material which may be appropriately joined together to form the luggage bag and, if desired a frame may be included over which the cover is attached.

Fastenings may, if desired, join adjacent portions of the wire mesh, which is generally has as strand of wire in a sinusoidal pattern, with the strand extending generally longitudinally and being turned back upon itself to form closed loops at each of the opposing edges of the wire mesh layer. Due to the construction of the mesh bag or sheet of the cover in this manner, when the wire mesh layer is in a relaxed state the wire mesh ends to collapse, closing the open spaces between the strands.

In many of the prior art wire mesh reinforced luggage bags the reinforcing cover or separate reinforcing sheets from which the luggage bag was assembled, were a composite reinforced textile, comprising inner and outer fabric bags laminated together to enclose the reinforcing wire mesh layer, or two layers laminated together with the mesh layer held therebetween. Such cover structures often included multi layer arrangements including the wire mesh layer and the various layers may be bonded together to provide additional desirable features to the luggage bag.

Bonding the wire mesh layer to the fabric layers by lamination, while effective to retain the wire mesh layer in place avoids the problems resulting from the mesh separating from the outer fabric layer and the liner fabric layer due to the tendency of the mesh to collapse. However, the manufacture of laminated luggage bags or sheets of cover material has proven to be relatively costly.

It is an object of the present invention to overcome or substantially ameliorate the above cost of lamination and the disadvantages inherent therein and, in general to provide an improved reinforced luggage bag in which the cover is a multi layer configuration providing an improved arrangement for securing the wire mesh layer to at least one of the fabric layers in the construction of softside luggage bags.

SUMMARY OF THE INVENTION

According to one aspect of the present invention there is provided a luggage bag having a reinforced cover and in which the cover is a multi layer configuration comprising a fabric layer and a reinforcing wire mesh layer with the strand of the wire mesh layer arrayed in a preselected pattern overlying a surface of the fabric layer. Stitching by a thread utilizing a preselected stitch, such as a lock stitch, extends lengthwise along the wire mesh layer and fixing the strand of the wire mesh layer to the fabric. In preferred embodiments of the present invention the strand forming the wire mesh layer is substantially continuous and comprises a metal strand. Optionally the wire mesh layer may comprise multiple strands, such as a metal wire, or other material including relatively high-strength strands, such as carbon fibers. As may be desired in particular applications, on a single sheet of the fabric layer, different lengths of the continuous reinforcing strand may be stitched to opposing sides, or separate reinforcing strands may be stitched to opposing sides of the fabric. A first fabric layer may cover the reinforcing wire mesh strand, and optionally, the first fabric layer may be bonded to a second fabric layer with the wire mesh layer, stitched to one of the fabric layers, contained therebetween.

In preferred embodiments of the present invention, the preselected pattern of the strands of the wire mesh layer comprises a net- or mesh-like pattern in which the strand of the wire mesh layer overlies itself it at intersections or nodes in the mesh-like pattern and, in the mesh-like pattern, the strand of the wire mesh layer is non-woven, and the strand is not looped, knotted, crimped or otherwise connected to itself at the intersections. That is, the strand of the wire mesh layer may overly itself at the nodes but the retention of the strand of the wire mesh layer on the fabric is by the aforementioned stitching.

In the preferred embodiments of the present invention, the stitching comprises a lockstitch, wherein one thread of the lockstitch crosses back and forth over the strand of the wire mesh layer and the other thread of the lockstitch extends longitudinally in the direction of the strand of the wire mesh layer.

The fabric layer may be woven, but it may alternatively be knitted. The reinforced textile comprising the fabric layer or layers containing the wire mesh may be utilized in the cover of a luggage bag and wherein there may be provided additional layers of other fabrics or materials as part of the cover in the construction of luggage bags. As such, it has been found advantageously to utilize the fabric layer or layers having the wire mesh layer stitched thereto as the lining for the inside of the luggage bag. The luggage bag may have, if desired, frame members on which the cover including the wire mesh layers is attached.

Another aspect of the present invention comprises a luggage bag in which the cover is fabricated from separate sheets and some, or all, of the separate incorporate the wire mesh reinforced composite sheet as described above.

The present invention also defines a method of manufacturing a reinforced composite sheet incorporating a wire mesh layer attached to a fabric layer and in which the wire mesh layer is sewn longitudinally along a continuous strand of the wire mesh to secure the wire mesh to a fabric layer in a pattern overlying a surface of the fabric. The sewing is performed by an embroidering machine which simultaneously feeds the wire mesh strand together with first and second threads, the first and second threads forming a lockstitch, the first thread crossing back and forth over the wire mesh strand, and the second thread extending longitudinally in the elongated direction of the wire mesh strand. Alternatively, in particular applications, other stitches may be employed to secure the wire mesh fabric strand to the fabric.

The wire mesh strand may be configured into a boustrophedonic pattern on the fabric layer the wire mesh strand having a plurality of sets of alternating first and second lengths of the strands, each strand having a wave shape and a common central axis and wherein the crests and troughs of adjacent sets overlap one another. AS a variation on such a configuration, the wire strand comprises a a plurality of alternating wire strand lengths each having a wave shape and the crests and troughs of adjacent portions of the strands overlap one another.

In another aspect the invention there is a method of reinforcing a fabric layer, comprising fastening an elongate reinforcement such as a strand of wire to a surface of fabric, the reinforcement wire strand following a boustrophedonic path having a plurality of sets of alternating first and second lengths of the strands of the wire mesh, each strand having a wave shape, and each first and second length of strand of the wire mesh having a common central axis, and wherein crests and troughs of adjacent sets overlap one another.

The invention also shows a method of reinforcing a fabric sheet, comprising the steps of: fastening an elongate wire strand in the form of a mesh to a surface of the fabric sheet, the strand following a boustrophedonic path comprising a plurality of alternating wire strand lengths, each wire strand length having a wave shape and a respective central axis, and wherein crests and troughs of adjacent wire strand lengths overlap one another.

The present invention also includes as a another embodiment a fabric layer and a reinforcing wire strand of a wire mesh layer that is arrayed in a pattern overlying a surface of the fabric layer and fixed to the fabric layer, the reinforcing wire strand following a boustrophedonic path comprising a plurality of sets of alternating first and second lengths of the wire strand, each wire strand length having a wave shape, the first and second length of each set having a common central axis, and wherein crests and troughs of adjacent sets overlap one another.

In another embodiment of the present invention there is provided, according to the invention, a reinforced sheet comprising a layer of fabric, a reinforcing strand of a wire mesh arrayed in a pattern overlying a surface of the fabric and fixed to a surface of the fabric layer, the reinforcing strand following a boustrophedonic path and comprising a plurality of sets of alternating lengths, each length having a wave shape, each length having a respective central axis, wherein crests and troughs of adjacent lengths of the wire strand of the wire mesh overlap one another.

The wave shape is substantially and the amplitude and frequency of the wave shape are substantially constant for a plurality of the lengths of the wire strand. The wire strand is continuous and is continuously, or intermittently as may be desired in particular applications, fastened to a surface of the fabric by one of stitching, adhesive and welding. As noted above, in preferred embodiments of the present invention, the stitching is a lock stitch contiguously fastening the wire mesh strand against the surface of the fabric in which one of the threads of the lock stitch crosses back and forth over the reinforcing wire strand, and the other thread of the lockstitch extends longitudinally in the direction of the reinforcing wire strand of the wire mesh.

In another embodiment of the present invention, the reinforcing strand may be enclosed in a tape, and the lock stitch connects the tape to a surface of the fabric.

If an adhesive is utilized to fasten the wire strand of the wire mesh to the fabric, the adhesive comprises a longitudinally continuous or intermittent adhesive bead bonding the wire strand to the fabric. In a variation of this embodiment the adhesive further comprises adhesive tape continuous with the reinforcing strand or a plurality of lengths of adhesive tape, wherein the reinforcing strand is bonded between the surface of the fabric and the adhesive tape.

In another embodiment of the present invention wherein, as noted above, a weld is utilized to secure the wire strand of the reinforcing wire mesh to a surface of the fabric, the reinforcing strand is coated in a fusible material and the welding comprises longitudinally continuous or intermittent ultrasonic welding of the fusible material to the fabric.

In the embodiments of the present invention, the wire strand is fabricated from a metal wire or other cut resistant material such as a hard carbon fiber, or the like. The wire strand may be a single filament wire or a conventional braided multiple wire.

According to the principals of the present invention, the luggage bag is comprised of an outer shell which may incorporate one or more layers of fabric, plastic or other desired material, and the the reinforced fabric layer with the wire mesh affixed thereto comprises a liner sheet of luggage bag with the surface of the reinforced fabric layer on the inside of the luggage bag and the reinforcing strands of wire are disposed between the fabric layer and the innermost layer of the shell. If desired, other layers may be placed on the surface of the reinforced fabric layer which is free of the wire mesh to provide, for example, another layer of water proofing material enclosing the storage volume of the luggage bag.

BRIEF DESCRIPTION OF THE DRAWINGS

The above and other embodiments of the present invention my be more fully understood from the following detailed description taken together with the accompanying drawing wherein similar reference characters refer to similar elements throughout and in which.

DESCRIPTION OF THE PREFERRED EMBODIMENTS

Figure 1:
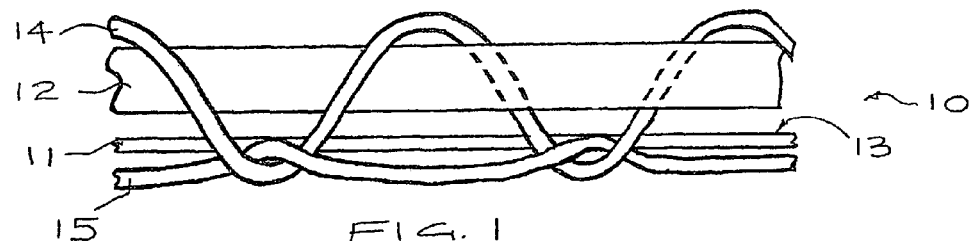
FIG. 1 is a partial semi-schematic sectional view through a fabric layer with a strand of a wire mesh secured to a surface thereof by a lock stitch.

Referring to FIG. 1, a reinforced textile 10 may be made from a sheet of fabric 11 to which a continuous reinforcing wire strand 12 of a wire mesh 7 is sewn. The reinforcing strand 12 overlies a surface 13 of the fabric 11 and is fixed to the fabric 11 by a lockstitch formed of an upper thread 14 and lower thread 15. The lockstitch may be a zigzag stitch in which the upper thread 14 crosses back and forth over the reinforcing wire strand 12, and the lower thread extends longitudinally in the direction of the reinforcing wire strand 12. The reinforcing strand 12 preferably comprises a multi-stranded metal wire, and the threads 14, 15 may comprise multi-filament threads. It will be appreciated that the illustration is schematic, and the scale and the space shown between the surface 13 and reinforcing wire strand 12, are not representative of the actual geometry.

Figure 2:
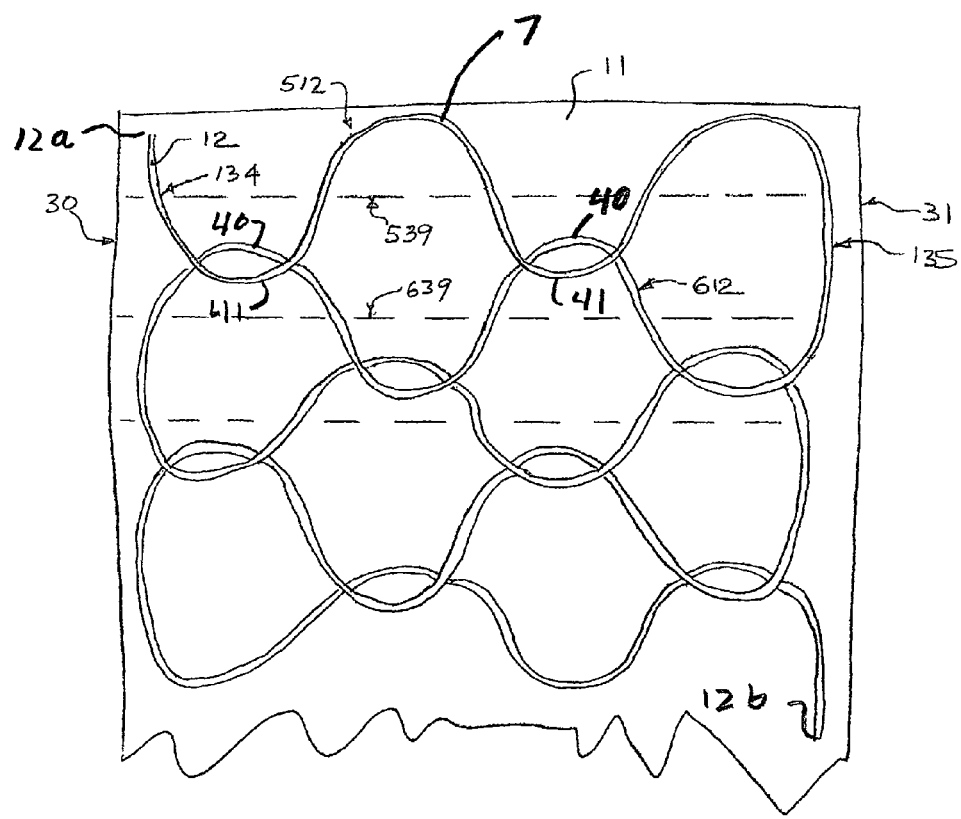
FIG. 2 is a partial semi-schematic plan view of the fabric layer of FIG. 1, showing a first preselected pattern of the reinforcing wire strand of the wire mesh.

As shown in FIG. 2, the reinforcing strand 12 of a wire mesh 7' may be one continuous length arrayed in a regular, mesh-like pattern and held by the threads 14, 15 (which are not shown in FIG. 2). The mesh-like pattern of FIG. 2 is of a first preferred type and may be formed with the reinforcing strand 12 extending in a wave-like form of constant frequency and amplitude, back and forth generally transversely in direction 21 between opposing edges 30, 31, the reinforcing wire strand 12 being turned back upon itself to form closed loops at each of the opposing edges of the fabric 11.

The reinforcing strand 12 is continuously fed, as from a reel (not shown), to an embroidering machine head (not shown) by which the reinforcing wire strand 12 is stitched to the panel. The embroidering machine head traces the mesh pattern of the wire strand while stitching and placing the reinforcing wire strand 12 at the same rate. The reinforcing wire strand 12 generally follows a boustrophedonic path extending back and forth between the edges 30, 31 and comprises lengths that alternate in direction. The first reinforcement length 512 extends left to right (with reference to FIG. 2), starting for instance at point 134 and extending to point 135 where it meets the second reinforcement length 612 that extends right to left, underlying the length 512 at nodes or intersections. The reinforcement wire lengths 512, 612 may have a substantially sinusoidal shape of the same amplitude and frequency. Reinforcement wire length 512 has a central axis 539 to either side of which the reinforcement wire length 512 extends, while reinforcement length 612 has a central axis 639 to either side of which the reinforcement length 612 extends. As FIG. 2 illustrates, the crests 40 and the troughs 41 of wave-shaped adjacent reinforcement wire lengths 512, 612 overlap one another, specifically the troughs 41 of length 512 overlap the crests 40 of the length 612. By overlapping the reinforcing strand 12 in the manner of FIG. 2, there is no path for a blade to pass between and separate the crests, unless the plane of the blade lies generally parallel to that of the textile 10, so the bag reinforced with this textile 10 is secured against being slashed open by a blade, even for a cut along a join in the mesh. The wire strand forming lengths 512 and 612 is continuous from a first end 12a to a second end 12b.

Figure 3:
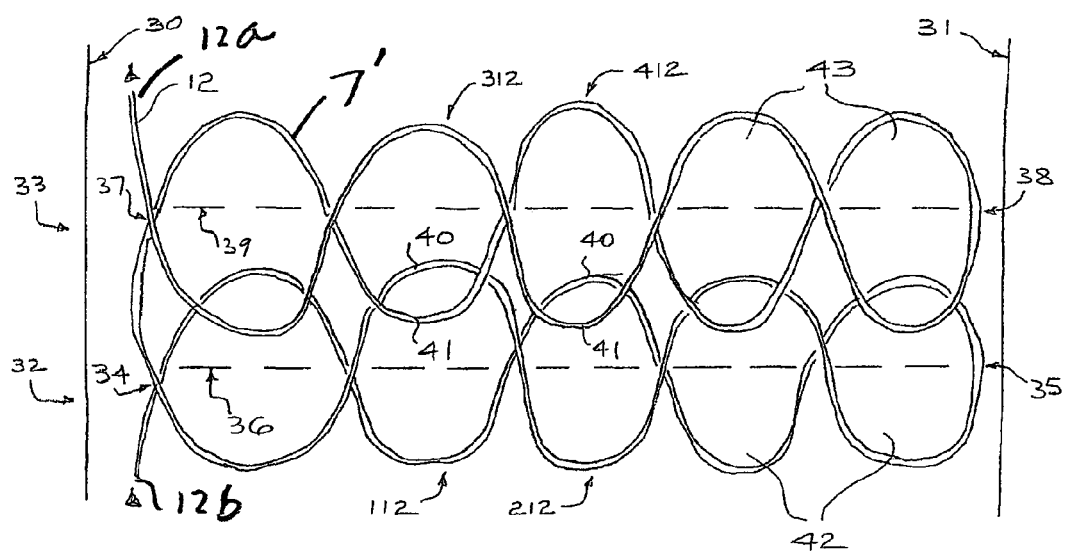
FIG. 3 is a partial semi-schematic plan view of the fabric layer of FIG. 1, showing a second preferred pattern of the reinforcing wire strand of the wire mesh.

FIG. 3 illustrates a second preferred method of reinforcing a fabric sheet with a reinforcing wire strand of a wire mesh pattern that extends between opposing edges 30, 31. The reinforcing strand 12 is continuously fed, as from a reel (not shown on FIG. 3), to an embroidering machine head (not shown on FIG. 3) by which the reinforcing strand 12 is stitched to the panel. The embroidering machine head traces the mesh pattern while stitching and placing the reinforcing strand 12 at the same rate. The reinforcing wire strand 12 is continuous from a first end 12a to a second end 12b and generally follows a boustrophedonic path extending back and forth between the edges 30, 31 and comprises first and second reinforcement wire lengths that alternate in direction and are arranged in a plurality of sets, two sets of which, sets 32 and 33, are shown in FIG. 3. Set 32 comprises reinforcement wire strand lengths 112, 212, while set 33 comprises like reinforcement lengths 312, 412 of the continuous reinforcing wire strand 12.

The first reinforcement length 112 of set 32 extends left to right (with reference to FIG. 3), starting for instance at point 34 and extending to point 35 where it meets the second reinforcement length 212 of set 32 that extends right to left, overlying the length 112 at nodes or intersections. The reinforcement lengths 112, 212 may have a substantially sinusoidal shape of the same amplitude and frequency, and a common central axis 36 to either side of which the reinforcement lengths 112, 212 extend. In this manner the resulting set 32 appears as a row of contiguous mesh openings or loops 42.

The set 33 is formed in a like manner from reinforcement wire strand lengths 312, 412 and appears as a row of contiguous loops 43. The first reinforcement length 312 of set 33 extends left to right, starting at point 37 and extending to point 38 where it meets the second reinforcement length 412 of set 33 that extends right to left, overlying the length 312 at nodes or intersections. The reinforcement wire lengths 312, 412 may have a like substantially sinusoidal shape extending either side of common central axis 39 at the same amplitude and frequency. As FIG. 3 illustrates, the loops 42, 43 of the sets 32, 33 overlap one another, more specifically the crests 40 of set 32 overlap the troughs 41 of set 33, the troughs 41 overlying the previously formed crests 40. It will be understood that the mesh pattern of FIGS. 2 and 3 can be varied to cover sheets of varying shapes, not only those which have parallel edges 30, 31 or which are rectangular. In particular, the shape of the loops 42, 43 adjacent the edges of the panel can be varied, so as to allow the reinforcing wire strand 12 to extend adjacent to such edges.

Figure 4:
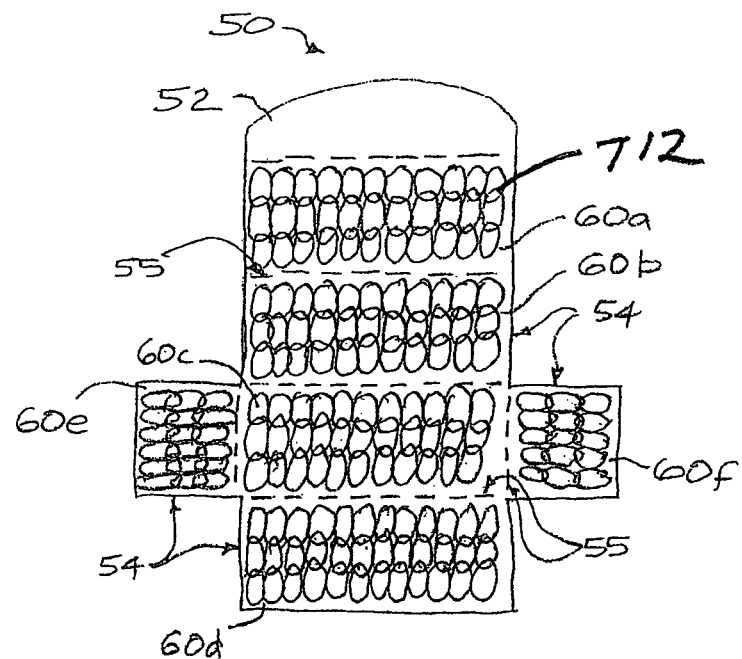
FIG. 4 illustrates a sheet of fabric cut to conform to the six orthogonal sides of a luggage bag with the fabric sheet having reinforcing strands of wire of a wire mesh as shown in FIG. 2 or 3 thereon.
Figure 5:
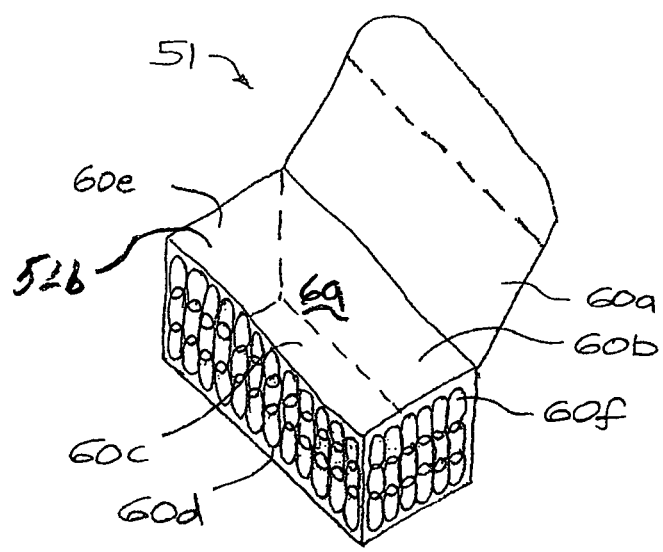
FIG. 5 illustrates fabric sheet of FIG. 4 folded along fold lines thereof for insertion into a luggage bag.

FIGS. 4 and 5 illustrate an exemplary construction of a reinforced liner for a liner bag, showing the flat pattern of the reinforced fabric layer 50 and as assembled into the reinforced fabric layer liner 51 respectively.

The flat pattern 50 may comprise the six orthogonal rectangular panels 60a-60f, each reinforced according to the invention with a wire mesh pattern, and formed on one side of a single sheet 52 of fabric. The wire mesh pattern may extend adjacent to, or contiguous with, the seams 54 and fold lines 55 (shown as broken lines) of each panel 60a-60f. As the reinforcing wire strand 12 stiffens the panels, terminating the mesh pattern adjacent to the seams 54 and fold lines 55 allows "sharper" corners to be formed along these edges than if the reinforcing strands themselves spanned across the seams or fold lines and thus had to be bent around the corners. In other arrangements of the present invention as may be desired for particular applications, the reinforcing wire strands of the wire mesh may extend over the fold lines 55. The liner 51 has the reinforcement wire strands of the wire mesh as indicated at 712 on panel 6a in the pattern shown on FIGS. 2 and 3 on the outer surface 52a of each of the sheets 6a-6f of the fabric 52 so as to be free of contact with the inner surface 52b. As shown on FIG. 5, the assembled sheets 6a-6f define the storage volume 69 of a luggage bag according to the principals of the present invention.

Figure 6:
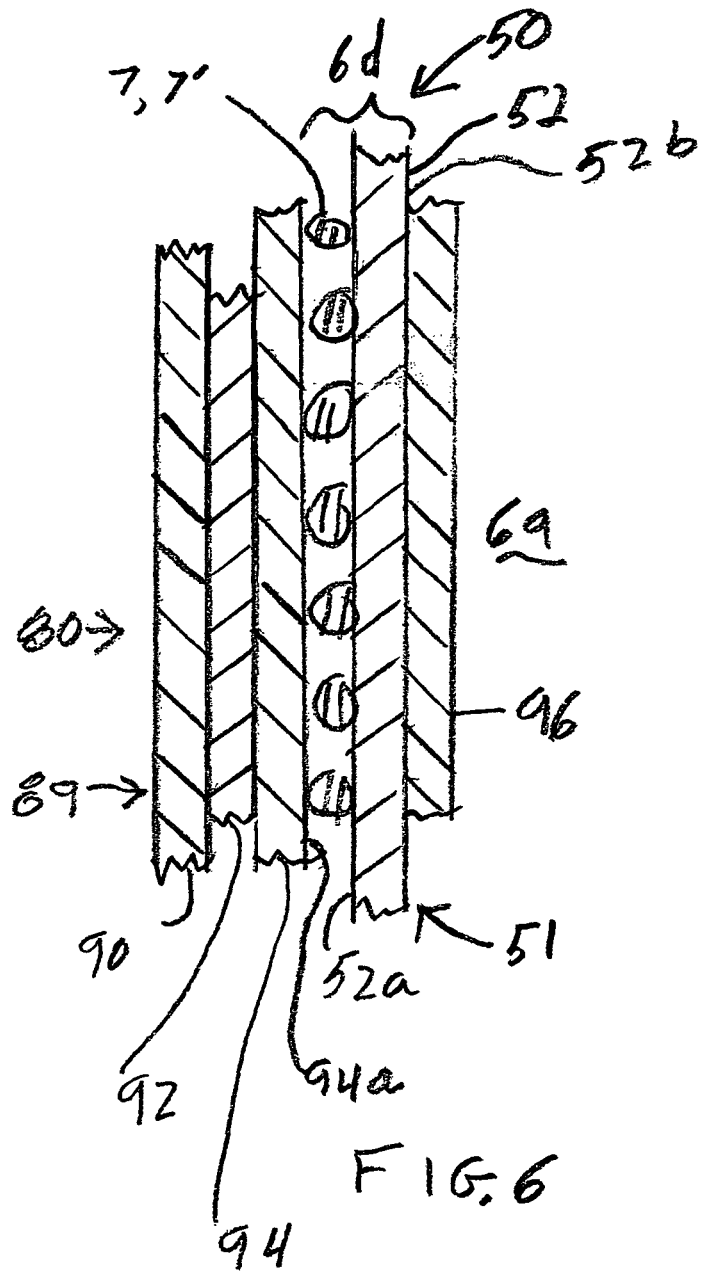
FIG. 6 is a partial sectional view through the wall of a luggage bag which incorporates the fabric sheet of FIG. 4.

FIG. 6 illustrates a partial sectional view through a wall 89 of a luggage bag 80 according to the principals of the present invention. As shown thereon, the wall 89 of the luggage bag 80 is a multi layer construction. The wall 80 has an exterior fabric layer 90 that is bonded to a protective layer 92. The protective layer 92 may be a sheet of polyethylene on the order of 0.4 mm thick. The protective layer 92 is bonded to a fabric mesh layer 94. The wire strand reinforced fabric layer 6d is placed inside the inner surface 94a of fabric mesh layer 94 For clarity, the threads holding the strands of the wire mesh layer 7, 7' are omitted from FIG. 6. If desired, an inner layer 96 may be inserted on the inside surface 52b of the fabric layer 52. The inner layer 96 may, for example, be a further waterproofing layer surrounding the storage volume 69. Depending on the application, one or more of the layers other than the fabric reinforced layer indicated may be omitted or, alternatively, other layers may be added for particular applications.

The invention claimed is:

1. A multi layer luggage bag having walls defining a storage volume, wherein at least one of the walls comprises a multi layers reinforced layer, the multi layers reinforced layer comprising:
   a sheet of fabric having an outer surface and an inner surface; and
   a reinforcing wire mesh having a wire strand arrayed in a preselected pattern and secured to said outer surface of said sheet of fabric by at least one of stitching, bonding and welding, the preselected pattern comprising lengths of wire strand extending transversely between opposite edges of the sheet of fabric, at least two adjacent lengths of wire strand are sinusoidal having crests and troughs that overlap each other and that have a sine waveform shape.

2. The multi layer luggage bag of claim 1 wherein the wire mesh is secured to said outer surface of said sheet of fabric by stitching, and said stitching is a zigzag lockstitch formed of an upper thread crossing back and forth over said wire strand, and a lower thread extending longitudinally along the direction of the wire strand.

3. The multi layer luggage bag of claim 1 wherein: said wire strand comprises a slicing cut resistant wire strand.

4. The multi layer luggage bag of claim 1 wherein: said preselected pattern of said wire mesh comprises a boustrophedonic pattern.

5. The multi layer luggage bag of claim 1 wherein: said crests and troughs of adjacent wire strand lengths are free of entanglement with each other.

6. The multi layer luggage bag of claim 1 wherein: said wire strand is comprised of one continuous wire strand having a first end and a second end and said lengths of said wire strand extending from said first end to said second end.

7. The multi layer luggage bag of claim 6 wherein: the wire mesh is secured to said outer surface of said sheet of fabric by stitching, and said stitching is a zigzag lockstitch formed of an upper thread crossing back and forth over said wire strand, and a lower thread extending longitudinally along the direction of the wire strand.

8. The multi layer luggage bag of claim 1 wherein the wire lengths having sinusoidal pattern have a constant frequency and amplitude.

9. The multi layer luggage bag of claim 1 wherein the wire strand comprises a single wire extending transversely between opposite edges of the sheet of fabric and wherein the wire strand is turned back upon itself at the edges of the sheet of fabric to form closed loops.

10. The multi layer luggage bag of claim 1 wherein two sinusoidal lengths of wire strand have a common axis.

11. The multi layer luggage bag of claim 1 wherein each sinusoidal length of wire strand has a unique central axis.

12. The multi layer luggage bag of claim 1 and further comprising an exterior fabric layer, the wire strand positioned between the sheet of fabric and the exterior fabric layer.

13. The multi layer luggage bag of claim 1 wherein the overlapping crests and troughs are spaced apart from one another.

14. The multi layer luggage bag of claim 1 wherein the wire strand is secured to the sheet of fabric along the length of the wire strand by stitching such that the wire strand cannot move relative to the sheet of fabric.

15. The multi layer luggage bag of claim 1 wherein: each of said walls of said luggage bag comprises a
   multi layers reinforced layer comprising:
      a sheet of fabric having an outer surface and an inner surface, said inner surface defining said storage volume; and
      a reinforcing wire mesh having a wire strand arrayed in a preselected pattern and secured to said outer surface of said sheet of fabric by at least one of stitching, bonding and welding.

16. The multi layer luggage bag of claim 8 wherein: the wire mesh is secured to said outer surface of said sheet of fabric in each of said walls of said luggage bag by stitching, and said stitching is a zigzag lockstitch formed of an upper thread crossing back and forth over said wire strand, and a lower thread extending longitudinally along the direction of the wire strand.

* * * * *